(12) United States Patent
Chishti et al.

(10) Patent No.: US 7,580,846 B2
(45) Date of Patent: Aug. 25, 2009

(54) METHOD AND SYSTEM FOR DISTRIBUTING PATIENT REFERRALS

(75) Inventors: Muhammad Chishti, Sunnyvale, CA (US); Kenneth Vargha, San Jose, CA (US); Joe Breeland, Austin, TX (US)

(73) Assignee: Align Technology, Inc., Santa Clara, CA (US)

( * ) Notice: Subject to any disclaimer, the term of this patent is extended or adjusted under 35 U.S.C. 154(b) by 1937 days.

(21) Appl. No.: 09/756,885

(22) Filed: Jan. 9, 2001

(65) Prior Publication Data

US 2002/0133386 A1 Sep. 19, 2002

(51) Int. Cl.
*G06Q 50/00* (2006.01)
(52) U.S. Cl. .................. 705/2; 705/3; 705/8; 707/104.1
(58) Field of Classification Search .............. 705/2, 705/3, 8; 707/104.1
See application file for complete search history.

(56) References Cited

U.S. PATENT DOCUMENTS

| | | | | |
|---|---|---|---|---|
| 5,225,976 A | * | 7/1993 | Tawil | ............................ 705/2 |
| 6,014,629 A | * | 1/2000 | DeBruin-Ashton | ............ 705/2 |
| 6,035,276 A | * | 3/2000 | Newman et al. | ................ 705/2 |
| 6,385,620 B1 | * | 5/2002 | Kurzius et al. | ........... 707/104.1 |
| 6,571,214 B2 | * | 5/2003 | Newman et al. | ................ 705/2 |
| 2001/0034639 A1 | * | 10/2001 | Jacoby et al. | .................. 705/10 |
| 2002/0032583 A1 | * | 3/2002 | Joao | ............................. 705/2 |
| 2002/0069085 A1 | * | 6/2002 | Engel et al. | ..................... 705/2 |
| 2002/0152096 A1 | * | 10/2002 | Falchuk et al. | ................. 705/2 |

OTHER PUBLICATIONS http://thehealthpages.com, Oct. 5, 1999.*

* cited by examiner

*Primary Examiner*—Gerald J. O'Connor
*Assistant Examiner*—Lena Najarian
(74) *Attorney, Agent, or Firm*—Townsend and Townsend and Crew LLP

(57) ABSTRACT

Practitioners are certified to perform a medical procedure, such as an orthodontic procedure. Certified practitioners are maintained in a referral directory and classified within tiers based on criteria such as the number of procedures that they have performed. Inquiries are solicited from prospective patients, and referral lists are provided to those patients who request them. The referral lists are obtained from the referral directory with doctors from higher tiers who have performed more procedures receiving preferential inclusion on the referral lists.

44 Claims, 3 Drawing Sheets

1. Dr. A. Loophole
   Address
   Phone No.

2. Dr. B. Twillie
   Address
   Phone No.

3. Dr. C. Sousé
   Address
   Phone No.

FIG. 3

METHOD AND SYSTEM FOR DISTRIBUTING PATIENT REFERRALS

BACKGROUND OF THE INVENTION

The present invention relates generally to business methods and more particularly to methods for referring practitioners certified to perform certain procedures to prospective patients.

Quality healthcare is a matter of overriding concern to the U.S. and worldwide populations. New medical and dental devices and procedures have been and will continue to contribute significantly to improvements in the quality of healthcare in the U.S. and abroad. Each new procedure is unique, and many new procedures and technologies require a learning period for the practitioner. For many such technologies, the creator of the technology, typically a company having a proprietary interest in the technology, will play a significant role in developing and disseminating the technology to practitioners. Frequently, the company will offer training to licensed doctors, dentists, and other health professionals, and will make "certification" resulting from such training a prerequisite to the dispensing and distribution of devices required to perform the new procedures.

Of particular interest to the present application, Align Technology, Inc., Santa Clara, Calif., has recently developed an orthodontic treatment system under the Invisalign® trade name. The Invisalign® System is dispensed to patients only by orthodontic practitioners who have been certified by Align to perform the new orthodontic procedure.

Align Technology, Inc., maintains an advertising campaign intended to inform patients of the availability and advantages of orthodontic treatment using the Invisalign® System. As part of the advertising campaign, potential patients are invited to contact Align by telephone or over the internet. As a result of such solicitation, Align receives many patient inquiries and is in a position to refer patients to individual practitioners.

In referring potential patients to individual practitioners, several objectives must be met. First, the referral process should be inclusive and assure that at least many of the practitioners who have been certified will receive referrals to assist them in developing their practices. It is also important, however, to avoid over loading relatively inexperienced practitioners who might otherwise benefit from additional time and patient experience to develop their skills in the new procedures. Finally, it would be advantageous to direct a larger number of potential patients to those practitioners who have demonstrated an ability to handle larger case loads and who have developed more skills and efficiencies in the new procedures.

For these reasons, it would be desirable to develop and implement new methods and procedures for referring patients to practitioners for performing novel and often proprietary medical procedures. Such methods and systems should provide referrals to most or all of the practitioners who have become certified to perform a new procedure but should preferentially direct referrals to those practitioners who are best able to handle a large number of patients. At least some of these objectives will be met by the inventions described hereinafter.

SUMMARY OF THE INVENTION

The present invention provides methods and systems for referring patients to practitioners who perform medical procedures. The medical procedures will typically be new and innovative procedures which are being introduced into the medical community by a company, organization, or institution which has developed the procedure and which usually has proprietary rights to the procedure. In this way, the company, organization, or other institution can maintain control over performance of the procedure, typically by controlling training of the practitioners as well as by dispensing and distributing of the tools, devices, and kits required to perform the procedures. An exemplary procedure for referral according to the present invention is an orthodontic procedure which is performed using the Invisalign® System available from Align Technology, Inc., Santa Clara, Calif. The procedure as well as the appliances used in the procedure are proprietary and described in U.S. Pat. No. 5,975,893, as well as the following pending U.S. patent applications:

| | | | | | |
|---|---|---|---|---|---|
| 09/466,353 | 09/298,268 | 09/454,786 | 09/454,278 | 09/483,071 | 09/169,276 |
| 09/169,036 | 09/169,034 | 09/313,291 | 09/264,547 | 09/313,290 | 09/311,941 |
| 09/311,716 | 09/311,715 | 09/539,185 | 09/539,021 | 09/534,461 | 60/199,485 |
| 60/199,662 | 60/199,663 | 60/199,610 | 60/199,465 | 09/616,222 | 09/506,419 |
| 09/560,052 | 09/557,382 | 09/566,424 | 09/576,721 | 09/621,716 | 09/620,253 |
| 09/626,192 | 09/641,208. | | | | |

The disclosures of the issued patent, as well as all pending applications, are incorporated herein by reference.

In a first aspect of the present invention, a method for referring patients to practitioners comprises certifying a group of practitioners to perform a medical procedure, such as an orthodontic procedure. Individual patients who wish to receive the procedure are identified, and the identified patients are provided with a referral list of certified practitioners. In order to assure that most patients are referred to practitioners who have significant experience in performing the procedure, the list preferentially includes and/or presents practitioners who have performed more procedures than other practitioners. Typically, the practitioners will be placed into "tiers" or levels which reflect the number of procedures performed, with those practitioners who have performed more procedures being assigned to higher tiers while those who have performed fewer procedures are assigned to lower tiers. The ability to direct or channel patients to experienced practitioners has a number of advantages. The majority of patients will be seen by practitioners who have significant experience and who have probably gained additional skills. Conversely, by directing or channeling fewer referral patients to those practitioners with less experience, those practitioners can gain experience without becoming overwhelmed with referrals. Additionally, those practitioners who have decided to emphasize or focus their practice on the procedure will benefit from a continuing referral base of patients interested in having the procedure performed.

Certification of the practitioners may be as simple as registering those practitioners who have a desire to perform the procedure. More usually, however, the practitioners will undergo education and/or training prior to certification. Such training will typically be provided by the company, organization, or other institution which sponsors the procedure, typically in the form of formal training sessions (e.g., seminars), written materials, electronic teaching materials, and presentations by a sales force, and the like. In addition to training, certification may require that the practitioners be tested, and in some instances it may be desirable to require that the practitioners perform at least one procedure, usually with a previously certified practitioner or trainer present.

Once certified, the names, addresses, and other contact information (such as phone number, facsimile number, e-mail address, and the like) will be collected for the practitioner and maintained in a referral directory. The referral directory will be updated periodically with new practitioners being added as they become certified. Of course, practitioners can be removed from the referral directory as well. Practitioners may be removed at their request or by action of the company, organization, or institution which maintains the referral directory. For example, should for any reason it become apparent that the practitioner has in the past, or continues to perform the procedure in an unacceptable fashion, the practitioner's name may be removed from the referral directory. The referral directory will also be updated with respect to status. For example, as practitioners perform additional procedures, the tier or other status designation may be upgraded. In instances where the sponsoring company or organization distributes the product necessary to perform the procedure, the number of procedures performed by an individual practitioner can be updated based on the number of kits, tools, or other products ordered by the practitioner from the sponsoring organization.

The referral directory will be organized in a manner which facilitates providing referrals information to individual patients. In particular, the referral directory will allow the sorting and retrieval of practitioners practicing in a given geographic area to facilitate matching of practitioners with the locations of prospective patients. For example, the referral directory may allow identification of doctors based on their addresses, zip codes, or the like, where that information can be matched with similar information from the prospective patient. From the geographic information, in most instances at least, a significant number of practitioners could be identified for any particular prospective patient. According to the present invention, however, the practitioners who are closer to the patient will be further selected so that the experienced practitioners who have performed more procedures are preferentially included on a referral list which is eventually provided to the patient. Usually, the practitioners will be arranged into tiers or levels based upon the number of procedures that they have performed. Practitioners may be randomly ordered within a tier or may further be ranked in a tier, typically based on the number of procedures performed. Usually, each tier will be defined by a threshold of a number of procedures performed over a selected period of time. Alternatively, the threshold number may be the cumulative or aggregate number of procedures performed by the practitioner measured from the time they began performing the procedure.

Usually, there will be at least three tiers to which the practitioners will be assigned. For example, practitioners may be assigned to an initial or lowest tier when they first become certified. After performing a certain threshold number of procedures, typically in the range from 5 to 25 during a calendar quarter, for the exemplary use of the Invisalign® System, practitioners may be assigned to an intermediate or next higher tier. The third or highest tier would then be achieved when the practitioner has performed a still higher threshold number of procedures, typically in the range from 10 to 50 procedures during a calendar quarter. Of course, there could be fourth, fifth, and even higher tiers, each of which would have a still higher threshold number of procedures defining its entry level.

In a second aspect, methods according to the present invention for referring patients to dental practitioners comprise certifying the dental practitioners to perform a dental procedures, such as the orthodontic procedure using the Invisalign® System described above. The method further comprises informing a potential patient population of the availability of the procedure, typically through advertising in the print and electronic media. Individual patients who are identified are provided with a referral list of certified practitioners, where the practitioners are placed on the referral lists based on one or more performance criteria, typically including at least the number of procedures performed. The number of procedures performed may be determined over a preselected or fixed time period or alternatively may represent the cumulative or aggregate number of procedures performed by the practitioner. The certification process has generally been described above. The practitioners are preferentially placed on the referral lists typically utilizing a tiering approach as described above. Individual patients will usually contact a referral center either by telephone, e-mail, or other electronic communication system.

In a third aspect of the present invention, methods for referring patients to practitioners comprise maintaining a referral directory, soliciting and receiving inquiries from prospective patients, and referring to individual patients practitioners from the referral directory that are located within the patient's geographic area. As described previously, the listing of practitioners in the referral directory will usually be prioritized into a plurality of tiers, typically at least three, depending on the number of procedures that each practitioner has performed. Maintaining the referral directory comprises certifying practitioners to perform the procedure, tracking the number of times each certified practitioner performs the procedure to produce a performance number for that practitioner, and periodically updating the referral directory to reflect updated performance numbers. As before, the performance numbers can either be based on the cumulative or aggregate number of procedures performed, but will more usually be based on the number of procedures performed by an individual practitioner over a predetermined time interval.

Soliciting typically comprises advertising and providing contact information that permits a prospective patient to contact a referral center. The referral center may be staffed by people who answer telephones or respond to electronic communications or may be provided by an automated response system, such as a telephone or web-based system which allows a patient to navigate through the system using a series of menus and prompts. Referring will comprise first determining a patient's geographic area and then generating from the referral directory a referral list of practitioners within the patient's geographic area. Usually, the list will include a plurality of practitioners from the geographic area, where the practitioners are selected and/or arranged so that practitioners from the higher tiers are preferentially presented relative to practitioners from a lower tier. The preference can be that the practitioners from higher tiers are listed more frequently, i.e., on more referral lists, than practitioners from lower tiers. Alternatively or additionally, practitioners from higher tiers may be placed more prominently on a referral list, e.g., usually at the beginning of the list rather than near an end of the list. By providing such preferential listings, it is expected that the practitioners on higher tiers who have performed more procedures will be contacted by more prospective patients as a result of the referral process than will practitioners from lower tiers.

In other cases, referring may comprise determining the location of the patient's geographic area and then selecting a single practitioner to be referred to the patient. In that case, the practitioners from higher tiers will be selected more frequently than those from lower tiers, thus again causing the practitioners from higher tiers to receive more referral calls from prospective patients. With both of these approaches, however, it may be preferred that all practitioners included in the referral directory will receive at least some calls (although in some instances the practitioners in the lower tiers may only receive referrals when no practitioners from higher tiers are present in a patient's geographic area). It may be advantageous that the practitioners from the lower tiers receive referrals (although in lesser number or at a lower rate) to give them the opportunity to gain experience in the procedure with less likelihood that they will be overwhelmed with referrals and new patients desiring to have the procedure. Additionally, those practitioners in the lower tiers who choose to do so may make an effort to work with both the referred patients as well as patients from other referral sources in order to increase the number of procedures that they perform and are in a higher tier in which case they will receive more referrals.

In yet another aspect of the present invention, a computer system having a processor and memory for generating a list of medical practitioners for referring to potential patients comprises a means for maintaining a referral directory and a means for sorting practitioners on the referral directory to produce a referral list. The means for maintaining a referral directory will include contact information for practitioners who are certified to perform the procedure wherein the practitioners are prioritized in a plurality of tiers depending on the number of procedures that they have performed. The means for sorting produces a referral list in response to an inquiry from a prospective patient wherein practitioners are first selected based on proximity to the geographic area of the patient. The practitioners are further preferentially selected based on the tier to which the practitioner has been assigned. As described above, the referral list may include a plurality of practitioners where the practitioners from the higher tiers may be included more often (or in some cases exclusively) on lists and/or included more prominently on lists, i.e., placed higher on a list than a practitioner in the same area but from a lower tier. Alternatively, the referral list may include only a single practitioner, where practitioners from the same geographic areas but from higher tiers are included on more lists than those from lower tiers. A computer system will further comprise means for inputting data into the maintaining means and means for displaying the referral lists. In a specific example, the display means is a visual display means which is useful for human operators manning telephone call centers. The computer system may be used as a part of a web-based system for automatically producing referral lists for prospective patients who choose to contact the provider over the web.

BRIEF DESCRIPTION OF THE DRAWINGS

FIG. 3 illustrates a referral list generated in accordance with the principles of the present invention as it might be shown on a visual monitor of the computer system of FIG. 2.

DESCRIPTION OF THE SPECIFIC EMBODIMENTS

The present invention for selecting and referring prospective patients to practitioners to will be described with respect to a method and system for orthodontics as described in U.S. Pat. No. 5,975,893, the full text of which has been previously incorporated herein by reference. The methods and systems described in that patent are now commercially available under the Invisalign® System trade name from Align Technology, Inc., Santa Clara, Calif. Briefly, certified orthodontic practitioners obtain an impression of the patient's teeth, usually both upper and lower jaws, which is then scanned or otherwise processed to produce a digital data set representing the initial position of the teeth. From that data set, Align Technology generates a final data set representing a desired tooth configuration which is based upon a prescription received from the orthodontic practitioner. After confirming the final tooth arrangement with the orthodontic practitioner, Align then models and produces a plurality of aligners which are polymeric shells which may be placed upon the teeth. Each of the successive aligners has a slightly different geometry selected to move the teeth toward their desired final positions. From between 20 and 60 aligners are normally used in any single course of treatment. The Invisalign® System is proprietary, and Align Technology certifies orthodontic practitioners to practice using the system. Align Technology will distribute and dispense the Invisalign® System only through those orthodontic practitioners who have been certified by Align to perform the procedure. While the present invention will be described with respect to the Invisalign® System, it will be appreciated that the methods and systems of the present invention will be useful with a variety of other medical procedures and systems where a company, organization, or other institution is in a position to certify practitioners and/or control the distribution and dispensing of the system to the practitioners.

Figure 1:
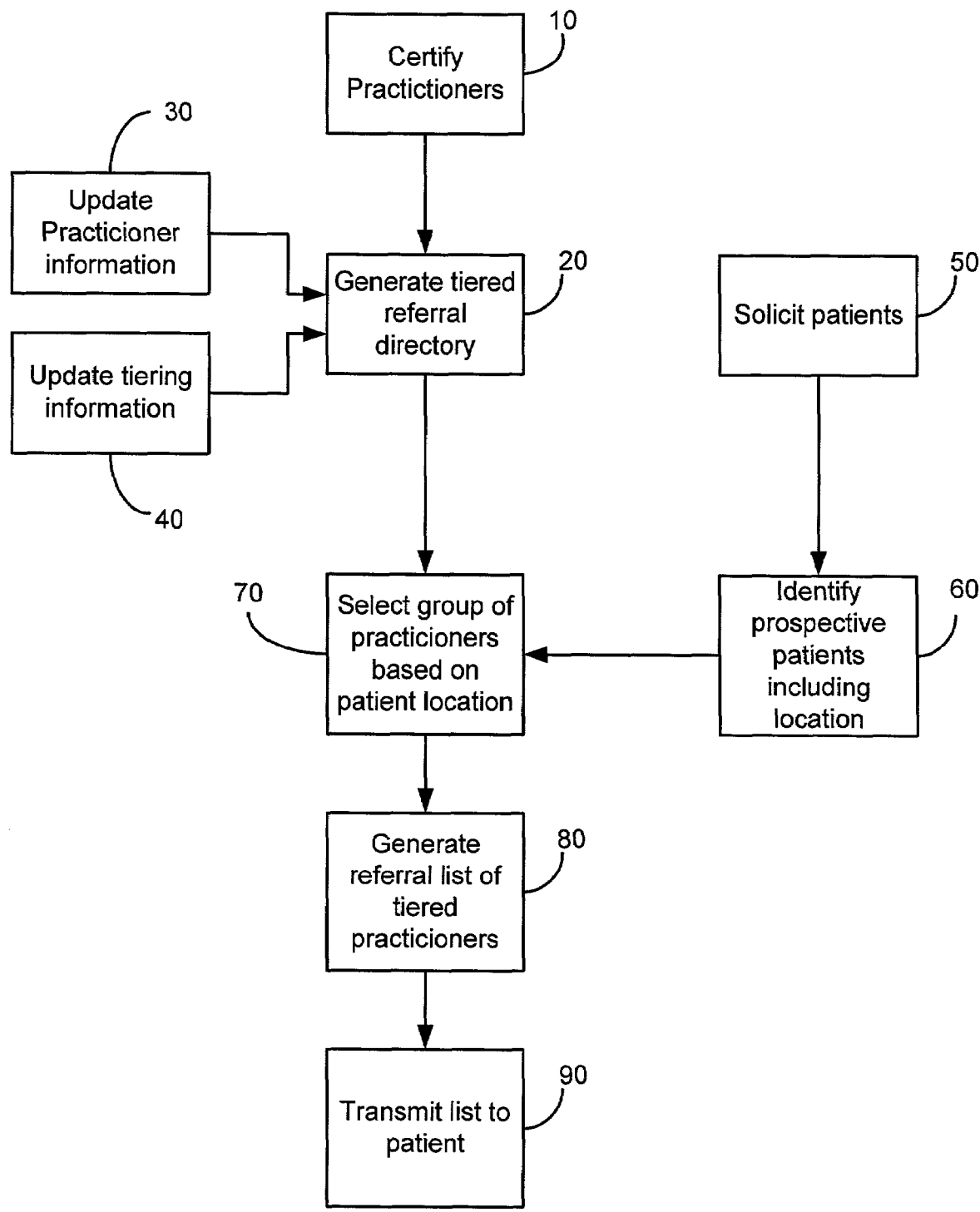
FIG. 1 is a block diagram illustrating the flow of information in the methods and systems of the present invention.

Referring now to FIG. 1, the present invention begins with the certification of practitioners as indicated at box 10. The practitioners will usually be orthodontists and the certification process will usually require attendance by the practitioner at a course where the details of the procedure are taught. Certification, however, could require more, e.g., testing, performance of at least one procedure under the guidance of a previously certified practitioner or teacher, or the like. Alternatively, certification could require mere registration if the procedure involved were not particularly complex and did not require specific training. As described elsewhere, however, the present method and system are particularly useful for relatively complex procedures which required training.

Once an initial group of practitioners has been certified, identification and contact information from each of the certified practitioners may be collected into a referral directory. The referral directory will usually be maintained as part of an electronic data base, permitting relatively easy access, updating, and manipulation, as described in more detail below. The referral directory will be updated as additional practitioners are certified and as practitioners are removed, if for any reason that should be necessary. Performance criteria, e.g., numbers of procedures and/or tiering, will also be updated over time as the practitioners gain experience.

The methods of the present invention rely on the preferential referral of certified practitioners based on a performance criteria, typically the number of procedures that that practitioner has performed. For all the reasons discussed above, it is believed that referring the greatest number of patients to practitioners who have the most experience and are likely the most efficient will be beneficial both to the patient and to the practitioner. Once the referral directory has been generated, such preferential referrals to patients can be effected in a variety of ways. Most simply, the referral directory could include the number of procedures which have been performed by an individual practitioner to date or over a specified prior period. More referrals could then be given to the practitioners who have achieved higher performance numbers than those who have achieved lower performance numbers. Usually, however, it will be more manageable to create "tiers" or levels within the referral directory, as shown in block 20. Successively higher tiers can be achieved as any practitioner completes certain threshold numbers of cases. For example, for practice with the Invisalign® System, an initial tier would include those practitioners who have been certified but who have completed fewer than a first threshold number of cases, usually in the range from 5 cases to 25 cases during a calendar quarter. Alternatively, the first threshold number could be a cumulative or aggregate number, typically in the range from 25 cases to 100 cases. Once a practitioner has exceeded this first threshold number of cases, the practitioner will enter the second tier, where that practitioner will remain until completing a second threshold number of cases. For the Invisalign® System, the second threshold will typically be from 10 cases to 50 cases over a calendar quarter, or from 50 cases to 200 cases measured cumulatively. After exceeding the second threshold number, the practitioner will be in the third or highest tier. Of course, any number of additional tiers could be created if there is a reason to do so.

While the above three-tiered scheme is particularly suitable for referring doctors using the Invisalign® System, the protocols can vary widely for other dental and medical procedures. For example, in some instances, it may be desirable to tier or grade the doctors based on some objective or subjective measure of their ability. For example, doctors who have been recognized as being particularly skilled in performing the subject procedure can be placed in higher tiers compared to doctors who are just beginning to learn the procedure. In other instances, it may be appropriate to tier doctors, at least in part, based on an individual doctor's expressed desire to perform more or fewer procedures. Additionally, in some instances, it may be desirable to tier doctors based on the availability of specialized equipment to perform the procedure and/or the size or availability of staff or other support to assist the doctor in performing the procedures. Of course, any two or more of these particular criteria can be combined and considered in assigning a doctor to a tier or level within the patient referral methods of the present invention.

The tiered referral directory, shown in block 20, will not be a static listing. Instead, it will be up-dateable to permit the addition of practitioners as well as the updating of individual practitioner information (block 30), such as new addresses, telephone numbers, web addresses, or the like. The tiered referral directory will also be updated as individual practitioners complete additional cases and move upward through the tiered levels (block 40).

The methods of the present invention also rely on soliciting patients (block 50), at least some of whom are subsequently referred to practitioners listed in the tier referral directory. A patient's solicitation will be through print or electronic advertising where the patients will be invited to contact a referral center. The referral center will usually have human operators who can answer telephone inquiries, e-mail inquiries, and the like. Alternatively, the referral center could comprise an automated response system which would reply to telephone inquiries based on a prerecorded menu and prompt system or could simply reply to internet or e-mail inquiries in an automated fashion. In addition to providing information to prospective patients, the referral center will obtain contact information from those prospective patients who express a desire to either receive general information or more specifically to receive a referral list including certified practitioners in their geographic area (block 60). Thus, it will be necessary to obtain information concerning the patient's location. Typically, an address or just a zip code of either the either the patient's home address or work address will be sufficient (although it may be necessary to get a postal or electronic address to send lists and/or other information).

The present invention will select practitioners based on the patient's location (block 70) and will generate a referral list of certified practitioners for those prospective patients who desire one. The referral list first identifies a group of practitioners who practice within a reasonable distance of the patient's location. Usually, this can be determined based upon zip code. Once the group of conveniently located practitioners has been generated, typically but not necessarily including all certified practitioners within a reasonable distance of the patient, the present invention will preferentially select among those practitioners to produce the referral list (block 80).

Usually, the referral list will include a plurality of practitioners, typically from one to 25, or typically from three to 15. If fewer than the target number of practitioners are present within a reasonable distance of the patient, then the referral list can simply include all practitioners who are within a requisite distance from the patient. Assuming, however, that more practitioners are close to the patient than are to be included on the referral list, it becomes necessary to select practitioners for the referral list for that individual patient.

Exemplary rules that can be applied to practitioner selection are as follows. A computer system which maintains the referral list can be programmed to receive locational information, such as address or zip code, of a prospective patient. Based on that locational information, the computer can select and order practitioners based on the following rules. First, all of the highest-tiered doctors who are closest to the patient, e.g., within five miles, can be retrieved from the list. Next, all of the highest-tiered doctors located within a next distance range from the patient, e.g., five to ten miles can be retrieved. Then, all of the next highest-tiered doctors within some distance from the patient can be selected, e.g., within ten miles. Then all of the highest-tiered doctors within some further distance from the patient, e.g., from 10 to 20 miles can be selected. Next, all of the second highest-tiered doctors within a similar range, e.g., 10 to 20 miles can also be selected. The selection of practitioners could continue but usually will be terminated after a target number has been reached, e.g., from three to 25, usually five to 10. Each of the retrieved groups of doctors can then be presented in a listing in order. Usually, doctors within each grouping, e.g., the highest-tiered doctors who are closest to the patient, will be randomly ordered and/or the order will be chosen so that the same doctors will not always appear first on the list provided to the patient. Similar randomization and/or selection of the doctors in each of the subsequent groupings will also take place.

Additional rules which may be employed and generating the patient referral lists include the following. First, there will usually be a maximum number of doctors generated for any particular patient, e.g., 15. This number, of course, can vary widely. If the search protocol described above fails to identify any doctors, or fails to identify an adequate number of doctors, then lower-tiered doctors within some preselected distance of the patient can then be provided on or added to the patient referral list. Optionally, the search can be stopped at some maximum distance from the patient's location, e.g., 200 miles. This practitioner selection protocol can be used both in fully automated systems, e.g., automated responses to inquires made over the company's website, or may be provided on computer screens which permit human operators to give information to prospective patients over the phone. Of course, the information could be provided via e-mail, facsimile, or other electronic means if desired. Additionally, both the human-operated and automatic website systems will usually allow prospective patients to search for practitioners by name to determine both their locations and whether they have been certified to perform the procedure.

After the referral list is generated, as shown in block 80, the list will be transmitted to the patient (block 90). If the patient has telephoned a call center, a list will usually be presented to an operator on a screen and may be simply read to the patient. In other instances, the list may be transmitted electronically, typically via e-mail, faxed, or sent by regular mail. The referral list will usually include at a minimum, the name of the practitioner, as well as address and contact information, such as telephone number, e-mail address, or the like.

Figure 2:
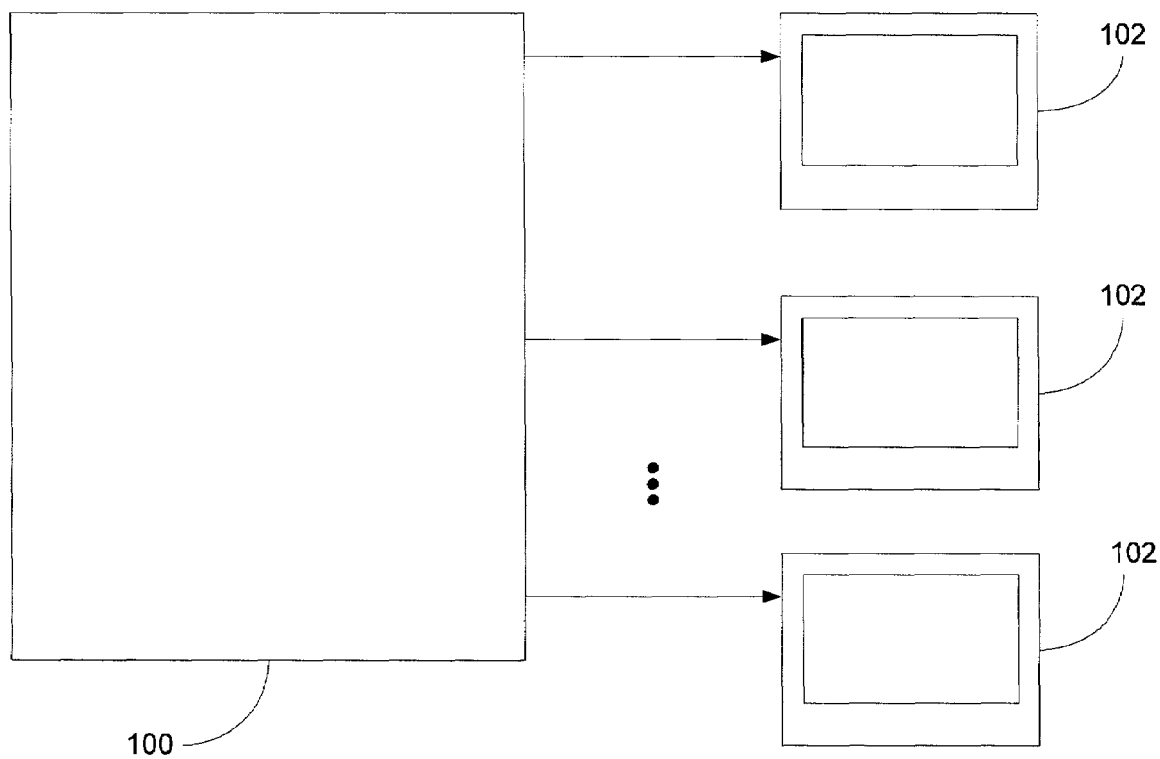
FIG. 2 is a schematic illustration of a computer system adapted for practicing the methods of the present invention.

Referring now to FIG. 2, systems according to the present invention will comprise a computer 100 which is typically networked to a plurality of remote computers or monitors 102. The computer will include normal hardware such as a processor, internal memory, input devices, such as an internal hard disc, external floppy disc, CD-ROM, and the like, typically being a networked system where computer 100 may comprise a server and computers/monitor 102 are connected to the server using conventional networking software. The computer will be adapted to store the referral directory of certified practitioners. The computer will still further be adapted to permit updating of the referral directory from time to time, both to add new certified practitioners and to update and change the tiering information of the practitioners. The computer will still further be adapted to generate referral lists of the tier practitioners in response to inquiries, such as the input of patient locations. In such instances, the compute will apply the selection rules described above.

In use, an operator at one of the monitors 102 will receive an inquiry and input prospective patient information, including the patient location, typically at least a zip code. Based on the location information, the computer 100 will generate an ordered list of certified practitioners, as shown in FIG. 3. The operator may then verbally provide the information relating to the referral list to a patient, either over the phone, via e-mail, via facsimile, or by other suitable transmission means.

In other instances, of course, the computer may be adapted to communicate directly with prospective patients, either via the web or via an automated telephone system. In both cases, there will be no need to provide individual monitors for operators receiving calls. Instead the computer will receive an electronic inquiry in the form of menus and prompts and provide an automated response. For web-based systems, the response will usually be a direct response to the inquiring patient over the web during the session initiated by the patient. For automated telephone systems, the reply will typically be via synthesized speech. In both cases, the responses could be confirmed and/or additional information provided by mail or facsimile. Both mail and facsimile responses can be automated based on the information received electronically from the prospective patient.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for referring patients to practitioners, said method comprising:
   certifying a group of practitioners to perform a medical procedure;
   identifying individual patients who wish to receive the procedure;
   accessing an electronic database having information comprising a number of procedures performed by each of the group of certified practitioners; and
   providing to the identified individual patients a list of certified practitioners, selected from the electronic database, wherein those practitioners who have performed more procedures than others of the practitioners are placed preferentially on the list.

2. A method as in claim 1, wherein certifying the practitioners comprises training practitioners.

3. A method as in claim 1 or 2, wherein certifying the practitioners comprises testing the practitioners.

4. A method as in claim 1 or 2, wherein certifying comprises requiring that the practitioners have performed at least one procedure.

5. A method as in claim 1, further comprising removing practitioners from the certified group.

6. A method as in claim 1, wherein the practitioners are placed into tiers based on the number of procedures performed and wherein practitioners from higher tiers are preferentially placed on lists.

7. A method as in claim 6, wherein the individual practitioners are randomly ordered within a tier.

8. A method as in claim 6 or 7, wherein each tier is defined by a threshold number of procedures performed over a selected period of time.

9. A method as in claim 6 or 7, wherein each tier is defined by the aggregate number of procedures performed.

10. A method as in claim 6, wherein the practitioners are assigned to at least three tiers.

11. A method as in claim 10, wherein the practitioners are assigned to an initial tier when they become certified, to an intermediate tier when they treat a first threshold number of patients over a preselected time period, and to a higher tier when they treat a second threshold number of patients over the preselected time period.

12. A method as in claim 1, wherein identifying individual patients comprises collecting names and contact information from individual patients.

13. A method as in claim 12, wherein at least some of the individual patients contact a coordinator in response to solicitations.

14. A method for referring patients to dental practitioners, said method comprising:
   certifying dental practitioners to perform a dental procedure;
   informing a potential patient population of the availability of the procedure;
   identifying individual patients who wish to receive the procedure;
   accessing an electronic database having information comprising performance criteria for each of the group of certified dental practitioners; and
   providing to the identified individual patients referral lists of certified practitioners, selected from the electronic database, wherein individual practitioners are preferentially placed on the referral lists based on one or more performance criteria.

15. A method as in claim 14, wherein the performance criteria include the number of dental procedures performed over a preselected time period.

16. A method as in claim 14 or 15, wherein the performance criteria include data relating to successful patient outcomes.

17. A method as in claim 14, wherein informing comprises soliciting patients.

18. A method as in claim 17, wherein soliciting comprises advertising in print and/or electronic media.

19. A method as in claim 14, wherein certifying the dental practitioners comprises training the dental practitioners.

20. A method as in claim 14 or 19, wherein certifying the dental practitioners comprises testing the dental practitioners.

21. A method as in claim 14 or 19, wherein certifying comprises requiring that the dental practitioners have performed at least one procedure.

22. A method as in claim 14, further comprising removing dental practitioners from the certified group.

23. A method as in claim 15, wherein the dental practitioners are placed into tiers based on the number of procedures performed and wherein the tiers are arranged in order on the list.

24. A method as in claim 23, wherein the individual dental practitioners are randomly ordered within a tier.

25. A method as in claim 23, wherein the dental practitioners are assigned to at least three tiers.

26. A method as in claim 23, 24, or 25, wherein each tier is defined by a threshold number of procedures performed over a selected period of time.

27. A method as in claim 23, 24, or 25, wherein each tier is defined by an aggregate number of procedures performed.

28. A method as in claim 25, wherein the dental practitioners are assigned to an initial tier when they become certified, to an intermediate tier when they treat a first threshold number of patients over a preselected time period, and to a higher tier when they treat a second threshold number of patients over the preselected time period.

29. A method as in claim 14, wherein identifying individual patients comprises collecting names and contact information from individual patients who contact a coordinator.

30. A method as in claim 29, wherein at least some of the individual patients contact a referral center who produces the referral list in response to solicitations from the coordinator.

31. A method for maintaining a referral directory, said method comprising:
certifying practitioners to perform a medical procedure;
tracking a number of times each certified practitioner performs the procedure; and
maintaining a patient referral directory in an electronic database having information comprising the number of times each certified practitioner has performed the procedure, wherein certified practitioners selected from the electronic database are prioritized on a list based on the number of times each certified practitioner has performed the procedure.

32. A method as in claim 31, wherein certifying the practitioners comprises training practitioners.

33. A method as in claim 31 or 32, wherein certifying the practitioners comprises testing the practitioners.

34. A method as in claim 31 or 32, wherein certifying comprises requiring that the practitioners have performed at least one procedure.

35. A method as in claim 31, further comprising removing practitioners from the certified group.

36. A method as in claim 31, wherein tracking comprises determining the number of times a practitioner acquires a kit to perform the procedure on a patient.

37. A method as in claim 31, further comprising dividing the directory based on geographic location.

38. A method as in claim 37, wherein the list is divided into at least two tiers with practitioners who have performed more than a first threshold number of procedures being in a higher tier.

39. A method as in claim 38, wherein the list is divided into at least three tiers with practitioners who have performed more than a first threshold number of procedures being in a higher tier, those who have performed more than a second threshold number but less than the first being in a lower tier, and those who have performed less than the second threshold number being in a still lower tier.

40. A method as in any of claims 32, 35, 36, 37, 38, or 39, wherein the number of times the procedure is performed is measured periodically over a fixed time interval and the directory periodically updated.

41. A method as in any of claims 32, 35, 36, 37, 38, or 39, wherein the practitioners are not ordered within a tier.

42. A method as in any of claims 32, 35, 36, 37, 38, or 39, wherein the practitioners are further ranked within each tier based on the number of procedures performed.

43. A method as in claim 31, wherein the directory is maintained in an electronic database.

44. A method as in claim 43, further comprising generating a referral list for an individual patient from the patient referral directory, wherein the listed is generated automatically from the electronic database based on the patient's geographic location and wherein practitioners with a higher priority have an increased likelihood of appearing on any referral list.

* * * * *

UNITED STATES PATENT AND TRADEMARK OFFICE
CERTIFICATE OF CORRECTION

| | |
|---|---|
| PATENT NO. | : 7,580,846 B2 |
| APPLICATION NO. | : 09/756885 |
| DATED | : August 25, 2009 |
| INVENTOR(S) | : Chishti et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2793 days.

Signed and Sealed this

Fourteenth Day of September, 2010

David J. Kappos
*Director of the United States Patent and Trademark Office*